United States Patent [19]

Schmidt et al.

[11] 4,377,576

[45] Mar. 22, 1983

[54] 5-(HETEROCYCLIC AMINO-PROPIONYL)-5,10-DIHYDRO-11H-DIBENZO[B,E][1,4]DIAZEPIN-11-ONES

[75] Inventors: Günther Schmidt, Biberach, Fed. Rep. of Germany; Mario Bergamaschi, Monza, Italy

[73] Assignee: Karl Thomae Gesellschaft mit beschränkter Haftung, Biberach an der Riss, Fed. Rep. of Germany

[21] Appl. No.: 282,501

[22] Filed: Jul. 13, 1981

[30] Foreign Application Priority Data

Jul. 24, 1980 [DE] Fed. Rep. of Germany ....... 3028001

[51] Int. Cl.³ ..................... A61K 31/55; C07D 243/38
[52] U.S. Cl. ............................. 424/244; 260/239.3 T
[58] Field of Search .................. 260/239.3 T; 424/244

[56] References Cited

U.S. PATENT DOCUMENTS 3,634,408 1/1972 Schmitt et al. ............... 260/239.3 T Primary Examiner—Robert T. Bond
Attorney, Agent, or Firm—Hammond & Littell, Weissenberger & Muserlian

[57] ABSTRACT

Compounds of the formula

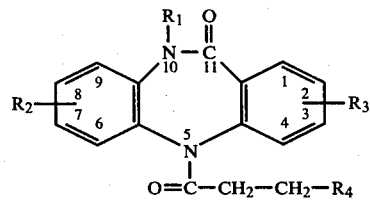

wherein
$R_1$ is hydrogen, methyl or ethyl;
$R_2$ is hydrogen or chlorine;
$R_3$ is hydrogen or chlorine; and
$R_4$ is pyrrolidino, piperidino, 2-methyl-piperidino, 2-ethyl-piperidino, 2,6-dimethyl-piperidino or morpholino;

and non-toxic, pharmacologically acceptable acid addition salts thereof. The compounds as well as their salts are useful as gastric secretion inhibitors and anti-ulcerogenics.

7 Claims, No Drawings

5-(HETEROCYCLIC AMINO-PROPIONYL)-5,10-DIHYDRO-11H-DIBENZO[B,E][1,4]DIAZEPIN-11-ONES

This invention relates to novel 5-substituted-5,10-dihydro-11H-dibenzo[b,e][1,4]diazepin-11-ones and non-toxic, pharmacologically acceptable acid addition salts thereof, to a method of preparing these compounds, to pharmaceutical compositions containing them as active ingredients, and to a method of using them as secretion inhibitors and anti-ulcerogenics.

More particularly, the present invention relates to a novel class of 5-substituted 5,10-dihydro-11H-dibenzo[b,e][1,4]diazepin-11-ones represented by the formula

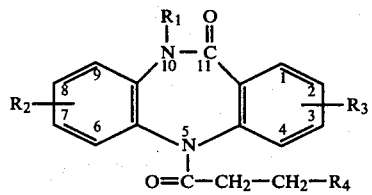

wherein
$R_1$ is hydrogen, methyl or ethyl;
$R_2$ is hydrogen or chlorine;
$R_3$ is hydrogen or chlorine; and
$R_4$ is pyrrolidino, piperidino, 2-methyl-piperidino, 2-ethyl-piperidino, 2,6-dimethyl-piperidino or morpholino;
and non-toxic, pharmacologically acceptable acid addition salts thereof.

The compounds embraced by formula I may be prepared by reacting a 5,10-dihydro-11H-dibenzo[b,e][1,4-]diazepin-11-one of the formula

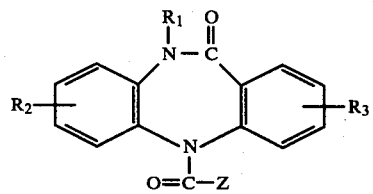

wherein
$R_1$, $R_2$ and $R_3$ have the same meanings as in formula I, and
Z is —$CH_2$—$CH_2$—Hal or —CH=$CH_2$, where Hal is halogen, especially chlorine or bromine,
with an amine of the formula

H—R$_4$    (III)

wherein $R_4$ has the same meanings as in formula I.

When Z in formula II is —$CH_2$—$CH_2$—Hal, the reaction is advantageously performed in an inert solvent, optionally in the presence of an acid-binding agent, at temperatures up to the boiling point of the reaction mixture. Preferred solvents are alcohols such as ethanol, n-propanol or isopropanol, ketones such as acetone, ethers such as dioxane or tetrahydrofuran, or also dimethylformamide; however, aromatic hydrocarbons such as benzene or toluene may also be used. The amine of the formula III is advantageously provided in molar excess, i.e. 2 mols of amine per mol of compound II, to neutralize the liberated hydrogen halide; however, other hydrogen halide-binding agents such as alkali metal carbonates or alkali metal bicarbonates, or tertiary amines such as triethylamine, pyridine or dimethylaniline may also be used for this purpose.

The reaction may also proceed by splitting off hydrogen halide and forming an intermediate of the formula II wherein the —CO—$CH_2$—$CH_2$—Hal group is converted into the acryloyl group which then undergoes an addition reaction with the amine of the formula III. In other words, under certain conditions the reaction of a compound of the formula II wherein Z is —$CH_2$—$CH_2$—Hal initially forms a compound of the formula II wherein Z is —CH=$CH_2$, which then reacts in situ with the amine of the formula III.

In analogy thereto, a compound of the formula I may also be prepared by first heating a solution of a compound of the formula II wherein Z is —$CH_2$—$CH_2$—Hal in an inert solvent, preferably at the reflux temperature of the reaction mixture, in the presence of an acid-binding agent to split off hydrogen halide, isolating the intermediate of the formula II wherein Z is —CH=$CH_2$ formed thereby, and subsequently reacting the intermediate in a suitable solvent with an amine of the formula III at temperatures up to the boiling point of the reaction mixture.

Examples of suitable inert solvents for the hydrogen halide cleavage step of the above reaction sequence are alcohols such as ethanol, high-boiling-point ethers such as dioxane or tetrahydrofuran, and aromatic hydrocarbons such as benzene or toluene. Examples of halogen halide-binding agents are alkali metal carbonates, alkali metal bicarbonates and tertiary organic amines such as triethyl-amine, pyridine or dimethylaniline.

Examples of suitable solvents for the reaction of the intermediate with the amine of the formula III are alcohols such as ethanol, n-propanol or isopropanol, ketones such as acetone, ethers such as dioxane or tetrahydrofuran, and aromatic hydrocarbons such as benzene or toluene.

The compounds of the formula I are basic and therefore form addition salts with inorganic or organic acids. Examples of non-toxic, pharmacologically acceptable acid addition salts are those formed with hydrochloric acid, hydrobromic acid, sulfuric acid, phosphoric acid, tartaric acid, fumaric acid, citric acid, maleic acid, succinic acid, oxalic acid or the like.

The starting compounds of the formula II may be prepared by reacting a 5,10-dihydro-11H-dibenzo[b,e][1,4]diazepin-11-one of the formula

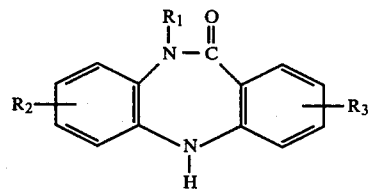

wherein $R_1$, $R_2$ and $R_3$ have the same meanings as in formula I, with a halopropionyl halide of the formula

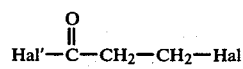

wherein Hal and Hal', which may be identical to or different from each other, are each chlorine, bromine or iodine, or with an acrylic acid halide of the formula

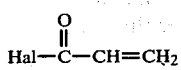  (VI)

wherein Hal is chlorine, bromine or iodine.

The reaction of a compound of the formula IV with a halopropionyl halide of the formula V yields the corresponding compound of the formula II wherein Z is —$CH_2$—$CH_2$—Hal.

The reaction of a compound of the formula IV with an acrylic acid halide of the formula VI yields the corresponding compound of the formula II wherein Z is —CH=$CH_2$.

The reaction of a compound of the formula IV with a compound of the formula V or VI is preferably carried out in an inert solvent, optionally in the presence of a hydrogen halide-binding agent, at elevated temperatures, preferably at the boiling point of the reaction mixture. Examples of suitable inert solvents are aromatic hydrocarbons such as benzene, toluene or xylene, ethers such as diethyl ether or dipropyl ether, or preferably cyclic ethers such as dioxane. Examples of suitable hydrogen halide-binding agents are tertiary organic amines such as triethylamine or N,N-dimethyl-aniline, pyridine, or inorganic bases such as alkali metal carbonates or alkali metal bicarbonates.

The reaction mixture is worked up in conventional manner, yielding up to 90% of theory of the desired end products. The 5-halopropionyl-substituted compounds of the formula II are in most instances well crystallizable substances which can be used in the subsequent reaction without further purification.

The following are examples of compounds of the formula II which were prepared by reacting a compound of the formula IV with a compound of the formula V, for example with 3-chloro-propionyl chloride in dioxane as the solvent:

(a) 5-(3-Chloro-propionyl)-5,10-dihydro-11H-dibenzo[b,e][1,4]diazepin-11-one, m.p. 217°–218° C.;
(b) 5-(3-chloro-propionyl)-5,10-dihydro-10-methyl-11H-dibenzo[b,e][1,4]diazepin-11-one, m.p. 181°–182° C. (decomp.);
(c) 2-chloro-5-(3-chloro-propionyl)-5,10-dihydro-10-methyl-11H-dibenzo[b,e][1,4]diazepin-11-one, m.p. 140°–142° C.;
(d) 2-chloro-5-(3-chloro-propionyl)-5,10-dihydro-11H-dibenzo[b,e][1,4]diazepin-11-one, m.p. 169°–171° C.;
(e) 5-(3-chloro-propionyl)-10-ethyl-5,10-dihydro-11H-dibenzo[b,e][1,4]diazepin-11-one, m.p. 133°–134° C.;
(f) 8-chloro-5-(3-chloro-propionyl)-5,10-dihydro-11H-dibenzo[b,e][1,4]diazepin-11-one, m.p. 235°–237° C.

The following is an example of a compound of the formula II which was prepared by reacting a compound of the formula IV with an acrylic acid halide of the formula VI:

(g) 5-(Acryloyl)-5,10-dihydro-11H-dibenzo[b,e][1,4]-diazepin-11-one, m.p. 255°–257° C. (decomp., from ethanol).

As mentioned above, the 5-(3-halo-propionyl)-5,10-dihydro-11H-dibenzo[b,e][1,4]diazepin-11-ones can easily be converted into the starting compounds of the formula II, wherein Z is —CH=$CH_2$, i.e. the starting compounds containing in 5-position an acryloyl group. Thus, for example, from 5-(3-chloro-propionyl)-5,10-dihydro-11H-dibenzo[b,e][1,4]diazepin-11-one in ethanol as the solvent, 5-(acryloyl)-5,10-dihydro-11H-dibenzo[b,e][1,4]diazepin-11-one, m.p.: 255°–257° C. (decomp., from ethanol), was obtained with a good yield after refluxing for 30 minutes in the presence of an excess of triethylamine. It is not necessary to isolate the acryloyl compounds from the reaction mixture; they can be directly reacted in the reaction mixture by addition of the corresponding amine of the formula III to form the desired end product of the formula I.

The compounds of the formula IV are known from the literature [see, for example, Hunziker, Arzneimittelforschung 13, 324 (1963) and British Pat. No. 1,236,112 (Thomae)].

The following examples illustrate the present invention and will enable others skilled in the art to understand it more completely. It should be understood, however, that the invention is not limited solely to the particular examples given below.

EXAMPLE 1

5,10-Dihydro-5-[3-(pyrrolidino)-propionyl]-11H-dibenzo[b,e][1,4]diazepin-11-one and its hydrochloride A mixture of 60.0 gm (0.2 mol) of 5-(3-chloropropionyl)-5,10-dihydro-11H-dibenzo[b,e][1,4]diazepin-11-one, 35.5 gm (0.5 mol) of pyrrolidine and 600 ml of isopropanol was refluxed for 45 minutes. After addition of activated charcoal, the reaction mixture was filtered, and the filtrate was evaporated in vacuo. The residue was stirred with water, and the crystalline product was suction-filtered off and recrystallized from isopropanol.

Yield: 55 gm of 5,10-dihydro-5-[3-(pyrrolidino)-propionyl]-11H-dibenzo[b,e][1,4]diazepin-11-one, m.p. 171°–173° C. This base was dissolved, while heating, in 200 ml of n-propanol, and the solution was admixed with the calculated amount of concentrated hydrochloric acid.

55.5 gm of the hydrochloride, m.p. 241°–243° C., were obtained. Yield: 75% of theory.

EXAMPLE 2

5,10-Dihydro-10-methyl-5-[3-(pyrrolidino)-propionyl]-11H-dibenzo[b,e][1,4]diazepin-11-one hydrochloride 4.5 gm (0.015 mol) of 5-(3-chloro-propionyl)-5,10-dihydro-10-methyl-11H-dibenzo[b,e][1,4]diazepin-11-one and 2.6 gm (0.0375 mol) of pyrrolidine were refluxed for 2 hours in 45 ml of isopropanol. The reaction mixture was worked up as described in Example 1.

3.9 gm of the hydrochloride, m.p. 235°–237° C. (recrystallized from isopropanol), were obtained.

Yield: 67% of theory.

EXAMPLE 3

2-Chloro-5,10-dihydro-5-[3-(pyrrolidino)-propionyl]-11H-dibenzo[b,e][1,4]diazepin-11-one 6.7 gm (0.02 mol) of 2-chloro-5-(3-chloropropionyl)-5,10-dihydro-11H-dibenzo[b,e][1,4]diazepin-11-one and 7.1 gm (0.1 mol) of pyrrolidine were refluxed in 50 ml of isopropanol for 2 hours. After addition of activated charcoal, the reaction mixture was filtered, and the filtrate was evaporated. The crystalline residue was recrystallized from aqueous 50% isopropanol.

4.3 gm of the title compound, m.p. 167°–169° C., were obtained.

Yield: 58% of theory.

EXAMPLE 4

2-Chloro-5,10-dihydro-10-methyl-5-[3-(pyrrolidino)-propionyl]-11H-dibenzo[b,e][1,4]diazepin-11-one 3.5 gm (0.01 mol) of 2-chloro-5-(3-chloro-propionyl)-5,10-dihydro-10-methyl-11H-dibenzo[b,e][1,4]diazepin-11-one and 3.5 gm (0.05 mol) of pyrrolidine were refluxed in 50 ml of dioxane for 4 hours. After addition of activated charcoal, the reaction mixture was filtered, and the filtrate was evaporated in vacuo. The residue was dissolved in chloroform, the solution was extracted with water, and the organic phase was evaporated in vacuo. The oily residue was obtained as crystals after addition of ether. After recrystallization from cyclohexane 2.6 gm of the crystalline title compound, m.p. 118°–120° C., were obtained.

Yield: 67% of theory.

EXAMPLE 5

5,10-Dihydro-5-[3-(piperidino)-propionyl]-11H-dibenzo[b,e][1,4]diazepin-11-one hydrochloride 60.0 gm (0.2 mol) of 5-(3-chloro-propionyl)-5,10-dihydro-11H-dibenzo[b,e][1,4]diazepin-11-one and 42.5 gm (0.5 mol) of piperidine were refluxed in 600 ml of isopropanol and worked up as described in Example 1. 53 gm of the hydrochloride (recrystallized from n-propanol), m.p. 250°–252° C., were obtained Yield: 69% of theory, M.p. of the base: 170°–172° C., recrystallized from isopropanol.

EXAMPLE 6

5,10-Dihydro-10-methyl-5-[3-(piperidino)-propionyl]-11H-dibenzo[b,e][1,4]diazepin-11one hydrochloride 6.3 gm (0.02 mol) of 5-(3-chloro-propionyl)-5,10-dihydro-10-methyl-11H-dibenzo[b,e][1,4]diazepin-11-one and 4.25 gm (0.05 mol) of piperidine were dissolved in 100 ml of dimethylformamide. After standing of the solution at room temperature for 60 hours, the precipitated piperidine hydrochloride was filtered off, the filtrate was evaporated in vacuo, the residue was dissolved in ethanol, the solution was adjusted to pH 2 with hydrochloric acid, and the solvent was distilled off in vacuo. The residue was recrystallized from ethyl acetate/isopropanol=1:1. 4.4 gm of the hydrochloride, m.p. 248°–249° C., were obtained.

Yield: 55% of theory.

EXAMPLE 7

2-Chloro-5,10-dihydro-5[3-(piperidino)-propionyl]-11H-dibenzo[b,e][1,4]diazepin-11-one 5.0 gm (0.015 mol) of 2-chloro-5-(3-chloropropionyl)-5,10-dihydro-11H-dibenzo[b,e][1,4]diazepin-11-one and 4.3 gm (0.05 mol) of piperidine were refluxed in 100 ml of dioxane for 1 hour. The reaction mixture was evaporated in vacuo, the residue was dissolved in dilute acetic acid, and the solution was filtered after addition of activated charcoal. The filtrate was made alkaline with ammonia and extracted with chloroform. The chloroform solution was evaporated in vacuo, and the residue was crystallized from isopropanol and recrystallized from methanol. 2.9 gm of the title compound, m.p. 170°–172° C., were obtained.

Yield: 50% of theory.

EXAMPLE 8

5,10-Dihydro-5-[3-(2-methyl-piperidino)-propionyl]-11H-dibenzo[b,e][1,4]diazepin-11-one hydrogen fumarate 9.0 gm (0.03 mol) of 5-(3-chloro-propionyl)-5,10-dihydro-11H-dibenzo[b,e][1,4]diazepin-11-one and 7.4 gm (0.075 mol) of 2-methyl-piperidine were refluxed in 200 ml of isopropanol for 4 hours. The reaction mixture was evaporated in vacuo, and the residue was purified on a silica gel column (eluant: chloroform+isooctane+methanol+ammonia−5+2+3+0.3). The resultant base (m.p. 156°–157° C., recrystallized from ethyl acetate) was dissolved by heating in ethyl acetate, admixed with fumaric acid, and evaporated in vacuo. The residue was recrystallized from ethyl acetate/methanol. 6.0 gm of the hydrogen fumarate, m.p. 140°–142° C., were obtained.

Yield: 42% of theory.

EXAMPLE 9

5,10-Dihydro-10-methyl-5[3-(2-methyl-piperidino)-propionyl]-11H-dibenzo[b,e][1,4]diazepin-11-one hydrogen sulfate 6.3 gm (0.02 mol) of 5-(3-chloro-propionyl)-5,10-dihydro-10-methyl-11H-dibenzo[b,e][1,4]diazepin-11-one and 5 gm (0.05 mol) of 2-methyl-piperidine were refluxed in 200 ml of isopropanol for 2 hours. The reaction mixture was evaporated in vacuo, the residue was dissolved in methylene chloride, and the solution was washed with water. The organic phase was evaporated in vacuo, the residue was dissolved in ethanol, and the solution was admixed with 4.5 gm of aqueous 30% sulfuric acid. The alcohol was partly distilled off, and the hydrogen sulfate was crystallized by adding ethyl acetate.

3.8 gm (40% of theory) were obtained.

M.p.: 215°–217° C.

EXAMPLE 10

5,10-Dihydro-10-ethyl-5-[3-(2-methyl-piperidino)-propionyl]-11H-dibenzo[b,e][1,4]diazepin-11-one hydrochloride 6.6 gm (0.02 mol) of 5-(3-chloro-propionyl)-5,10-dihydro-10-ethyl-11H-dibenzo[b,e][1,4]diazepin-11-one (m.p. 133°–134° C.) and 5 gm (0.05 mol) of 2-methyl-piperidine were refluxed in 100 ml of isopropanol for 2 hours. The reaction mixture was evaporated in vacuo, the residue was dissolved in methylene chloride, and the solution was washed with water. After evaporation of the solvent, the residue was dissolved in hot acetone, and the calculated amount of hydrochloric acid was added.

Yield: 4.3 gm (50% of theory) of the hydrochloride.

M.p.: 243°–244° C.

EXAMPLE 11

2-Chloro-5,10-dihydro-5-[3-(2-methyl-piperidino)-propionyl]-11H-dibenzo[b,e][1,4]diazepin-11-one 5.0 gm (0.015 mol) of 2-chloro-5-(3-chloro-propionyl)-5,10-dihydro-11H-dibenzo[b,e][1,4]diazepin-11-one and 5 gm (0.05 mol) of 2-methyl-piperidine were refluxed in 100 ml of dioxane for 2 hours and worked up as described in Example 7.

Yield: 3.3 gm (54% of theory) of the title compound (after recrystallization from isopropanol).

M.p.: 199°–201° C.

EXAMPLE 12

8-Chloro-5,10-dihydro-5-[3-(2-methyl-piperidino)-propionyl]-11H-dibenzo[b,e][1,4]diazepin-11one 11.5 gm (0.034 mol) of 8-chloro-5-(3-chloro-propionyl)-5,10-dihydro-11H-dibenzo[b,e][1,4]diazepin-11-one (m.p. 235°–237° C.) and 16.2 gm (0.16 mol) of 2-methyl-piperidine were refluxed in 100 ml of isopropanol for 1 hour. The reaction mixture was then evaporated in vacuo, the residue was dissolved in chloroform, the solution was washed with sodium hydroxide, and the organic solvent was distilled off in vacuo. The residue was recrystallized from xylene.

Yield: 12.0 gm (88% of theory).
M.p.: 201°–202° C. (decomp.)

EXAMPLE 13

5,10-Dihydro-5[3-(2-ethyl-piperidino)-propionyl]-11H-dibenzo[b,e][1,4]diazepin-11-one 6.0 gm (0.02 mol) of 5-(3-chloro-propionyl)-5,10-dihydro-11H-dibenzo[b,e][1,4]diazepin-11-one and 8.5 gm (0.075 mol) of 2-ethyl-piperidine were stirred in 100 ml of dimethylformamide at room temperature for 18 hours. The solvent was then distilled off in vacuo, and the residue was purified on a silicagel column (eluant:ethanol). The resulting base was recrystallized from ethyl acetate/ether.

Yield: 3.6 gm (48% of theory) of the title compound.
M.p.: 147°–148° C.

EXAMPLE 14

5,10-Dihydro-5-[3-(2-ethyl-piperidino)-propionyl]-10-methyl-11H-dibenzo[b,e][1,4]diazepin-11-one hydrochloride 8.5 gm (0.027 mol) of 5-(3-chloro-propionyl)-5,10-dihydro-10-methyl-11H-dibenzo[b,e][1,4]diazepin-11-one and 8.5 gm (0.075 mol) of 2-ethyl-piperidine were refluxed in 85 ml of n-propanol for 3 hours, and the reaction mixture was worked up as described in Example 10. After recrystallization from a mixture consisting of equal parts of dioxane and acetone, 6.8 gm of the hydrochloride were obtained.

Yield: 58% of theory.
M.p.: 209°–211° C.

EXAMPLE 15

5,10-Dihydro-5-[3-(2,6-dimethyl-piperidino)-propionyl]-10-methyl-11H-dibenzo[b,e][1,4]diazepin-11-one 6.3 gm (0.02 mol) of 5-(3-chloro-propionyl)-5,10-dihydro-10-methyl-11H-dibenzo[b,e][1,4]diazepin-11-one and 8.4 (0.075 mol) of 2,6-dimethyl piperidine were refluxed in 100 ml of isopropanol for 6 hours. The reaction mixture was worked up as described in Example 13. After recrystallization from ethyl acetate by addition of a little ether, 4.2 gm (54% of theory) of the title compound were obtained.

M.p.: 143°–145° C.

EXAMPLE 16

5,10-Dihydro-5-[3-morpholino-propionyl]-11H-dibenzo[b,e][1,4]diazepin-11-one 6.0 gm (0.02 mol) of 5-(3-chloro-propionyl)-5,10-dihydro-11H-dibenzo[b,e][1,4]diazepin-11-one and 10 gm (0.11 mol) of morpholine were refluxed in 200 ml of isopropanol for 2 hours. The solvent was distilled off, the residue was dissolved in methylene chloride, and the solution was washed with water. After distilling off the solvent, the residue was recrystallized from isopropanol.

Yield: 3.9 gm (56% of theory).
M.p.: 183°–184° C.

EXAMPLE 17

5,10-Dihydro-10-methyl-5-[3-morpholino-propionyl]-11H-dibenzo[b,e][1,4]diazepin-11-one hydrochloride 6.3 gm (0.02 mol) of 5-(3-chloro-propionyl)-5,10-dihydro-10-methyl-11H-dibenzo[b,e][1,4]diazepin-11-one and 10 gm (0.11 mol) of morpholine were refluxed in 200 ml of isopropanol for 3 hours. After distilling off the solvent, the residue was dissolved in methylene chloride, and the solution was washed with water and evaporated in vacuo. The residue was dissolved in ethanol, and the solution was adjusted to pH 4 with hydrochloric acid. The resulting hydrochloride was recrystallized from isopropanol.

Yield: 3.9 gm (49% of theory).
M.p.: 256°–257° C. (decomp.)

EXAMPLE 18

2-Chloro-5,10-dihydro-10-methyl-5-[3-morpholino-propionyl]-11H-dibenzo[b,e][1,4]diazepin-11-one 3.5 gm (0.01 mol) of 2-chloro-5-(3-chloro-propionyl)-5,10-dihydro-10-methyl-11H-dibenzo[b,e,][1,4]diazepin-11-one and 4.4 gm (0.05 mol) of morpholine were refluxed in 50 ml of dioxane for 4 hours. The reaction mixture was worked up as described in Example 12. After recrystallization from isopropanol by addition of a little ether, 2.5 gm (62% of theory) of the title compound were obtained.

M.p.: 138°–140° C.

EXAMPLE 19

5,10-Dihydro-5-[3-pyrrolidino-propionyl]-11H-dibenzo[b,e][1,4]diazepin-11-one

Preparation of the starting compound, 5-Acryloyl-5,10-dihydro-11H-dibenzo[b,e][1,4]diazepin-11-one (a) 5.0 gm (0.017 mol) of 5-(3-chloro-propionyl)-5,10-dihydro-11H-dibenzo[b,e][1,4]diazepin-11-one and 2.0 gm (0.02 mol) of triethylamine were refluxed in 250 ml of ethanol for 30 minutes. Subsequently, the reaction mixture was evaporated in vacuo, and the residue was stirred with water. After suction-filtering and drying, 5-acryloyl-5,10-dihydro-11H-dibenzo[b,e][1,4]diazepin-11-one was obtained with a quantitative yield. Recrystallization from ethanol.

M.p.: 255°–257° C. (decomp.).

(b) 5.26 gm (0.025 mol) of 5,10-dihydro-11H-dibenzo[b,e][1,4]diazepin-11-one and 2.7 gm (0.03 mol) of acrylic acid chloride were refluxed in 200 ml of toluene for 3 hours. Subsequently, the reaction mixture was evaporated in vacuo to dryness, and the residue was stirred with aqueous sodium bicarbonate solution. After suction-filtering, washing with water, and drying, 5-acryloyl-5,10-dihydro-11H-dibenzo[b,e][1,4]diazepin-11-one was obtained with a quantitative yield. Recrystallization from ethanol.

M.p.: 255°–257° C. (decomp.).

Preparation of the end product, 5,10-Dihydro-5-[3-pyrrolidino-propionyl]-11H-dibenzo[b,e,][1,4]diazepin-11-one 5.3 gm (0.02 mol) of 5-acryloyl-5,10-dihydro-11H-dibenzo[b,e][1,4]diazepin-11-one and 1.6 gm (0.022 mol) of pyrrolidine were refluxed in 200 ml of ethanol for 30 minutes. After addition of activated charcoal, the reaction mixture was filtered while hot, and the filtrate was evaporated in vacuo. The residue was recrystallized from a little ethyl acetate.

Yield: 5.7 gm (85% of theory).
M.p.: 171°–173° C.

EXAMPLE 20

5,10-Dihydro-5-[3-pyrrolidino-propionyl]-11H-dibenzo[b,e][1,4]diazepin-11-one 6.3 gm (0.03 mol) of 5,10-dihydro-11H-dibenzo[b,e][1,4]diazepin-11-one and 3.3 gm (0.036 mol) of acrylic acid chloride were refluxed, while stirring, in 200 ml of toluene for 3 hours. The reaction mixture was then evaporated in vacuo. The dry residue was admixed with 200 ml of ethanol, and 2.5 gm (0.035 mol) of pyrrolidine were added dropwise, while stirring, to the boiling solution. Subsequently, the reaction mixture was heated for 20 minutes, then evaporated in vacuo to about 1/10 of its original volume, and discolored by filtration through activated charcoal/silica gel. The crude product was recrystallized from a little ethyl acetate.

Yield: 8.8 gm (87% of theory).
M.p.: 171°–173° C.

The compounds of the present invention, that is, those embraced by formula I and their non-toxic, pharmacologically acceptable acid addition salts, have useful pharmacodynamic properties. More particularly, they exhibit anti-ulcerogenic and secretion-inhibiting activities in warm-blooded animals, such as rats.

The above pharmacodynamic properties of the compounds of the present invention were ascertained and compared to those of known, chemically related compounds disclosed in German Pat. No. 1,795,176 by the methods described below. The results of these tests for a few representative species of the present invention and the prior art are shown in the table below, where A = 5,10-dihydro-5-(3-pyrrolidino-propionyl)-11H-dibenzo[b,e][1,4]diazepin-11-one hydrochloride (see Example 1);

B = 5,10-dihydro-10-methyl-5-(3-pyrrolidino-propionyl)-11H-dibenzo[b,e][1,4]diazepin-11-one hydrochloride (see Example 2);

C = 5,10-dihydro-5-(3-piperidino-propionyl)-11H-dibenzo[b,e][1,4]diazepin-11-one hydrochloride (see Example 5);

D = 5,10-dihydro-5-(pyrrolidino-acetyl)-11H-dibenzo[b,e][1,4]diazepin-11-one (see German Pat. No. 1,795,176);

E = 5,10-dihydro-10-methyl-5-(pyrrolidino-acetyl)-11H-dibenzo[b,e][1,4]diazepin-11-one hydrochloride (see German Pat. No. 1,795,176); and F = 5,10-dihydro-5-(piperidino-acetyl)-11H-dibenzo[b,e][1,4]diazepin-11-one (see German Pat. No. 1,795,176).

The inhibiting activity on the gastric secretion was tested in male Crl:COBS (WI) BR Albino rats having a weight of 100 to 125 gm, according to the method of Shay et al., Gastroenterology 26, 906 (1954). The rats were fasted for 24 hours and then anesthetized with ether. The stomach was opened, and the pylorus was tied up. The compounds were administered intraduodenally immediately after the pylorus ligature in a constant volume of 0.2 ml/100 gm. 10 animals each were used per compound. The control animals received the same volume of the vehicle (0.2% methyl cellulose solution). After 4 hours the animals were killed by dislocating the neck vertebra, the stomachs were removed, opened along the great curvature and the gastric fluid collected. The free and total hydrochloric acid in the gastric fluid was measured by titration with N/10 sodium hydroxide solution. The results were determined in percent from the data received from the treated and untreated animals. The $ED_{50}$ values were calculated by linear regression analysis of the probits according to the method described by D. J. Finney, Probit Analysis, Cambridge University Press, 1971.

The inhibiting effect on the formation of stomach ulcers was tested in female Crl:COBS-CD(SD)Br rats having a weight of 130 to 160 gm, according to the method of P. A. Brown, European J. Pharmacol. 51, 275 (1978). The animals were fasted for 24 hours, and the compounds were suspended in a 0.2% methyl cellulose solution and administered to the animals using an esophageal tube. After 30 minutes the animals received acetyl salicylic acid perorally at a dose of 8 mg/kg, and after another 30 minutes the animals were placed at room temperature into a close-meshed wire cage. After one hour the animals were killed by dislocating the neck vertebra, the stomach was removed, opened by cutting along the great curvature, the inner side was outwardly spread out on a test tube, and the presence of stomach ulcers was recorded. The activity of the compounds was determined by counting the numbers of stomachs which were free of ulcers. The $ED_{50}$ was calculated according to the method described by J. T. Litchfield and F. Wilcoxon, J. Pharmac. Exp. Therap. 96, 99 (1949).

The effect on the size of the pupil was tested in male Crl:COBS-CD(SD)BR rats having a body weight of 100 to 130 gm by using a Nachet-binocular microscope with a graduated lens and a 10-fold magnification. The compounds were suspended in a 0.2% methyl cellulose solution and administered using an esophageal tube; groups of 5 animals were used per dose. The control animals received the same volume (1 ml/100 gm of body weight) of the vehicle. The diameter of the pupil was measured before administering the test compound, and 30, 60, 90 and 120 minutes after the treatment. The activity was expressed in percent with regard to the maximum diameter obtained by means of atropine. The $ED_{50}$ was determined by linear regression analysis of the probits according to the method described by D. J. Finney (supra).

The acute toxicity was determined in male CrL-COBS-CD-I(ICR) mice of an average body weight of 22 to 24 gm which had been fasted for 24 hours. Different doses of each compound were administered to groups of 5 to 10 animals by means of an esophageal tube, and the $LD_{50}$-values were calculated by the method of D. J. Finney (supra).

The following table shows the results which were obtained:

| Compound | Inhibition of gastric fluid secretion (liberation of acid) (Rat) $ED_{50}$ mg/kg i.d. | Ulcer Inhibition (Rat) $ED_{50}$ mg/kg p.o. | Mydriasis (Rat) $ED_{50}$ mg/kg p.o. | Acute toxicity (Mouse) $LD_{50}$ mg/kg p.o. |
|---|---|---|---|---|
| Invention: | | | | |
| A | 0.20 | 1.27 | 3.61 | 609 |
| B | 0.73 | 2.05 | — | 574 |
| C | 1.60 | 2.10 | 3.84 | 813 |
| Prior art: | | | | |
| D | 8.15 | 10.20 | 9.91 | 860 |
| E | 18.05 | 8.40 | 9.84 | 816 |
| F | 6.17 | 10.40 | 5.82 | 600 |

These results show that, in comparison to the structurally closely related prior art compounds, the compounds of the present invention are significantly more effective secretion and ulcer inhibitors without concurrent undesirable mydriatic side-effects.

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective oral dosage unit of the compounds according to the present invention is from 0.007 to 0.7 mgm/kg body weight, preferably 0.014 to 0.14 mgm/kg body weight; the daily dose is 0.014 to 1.4 mgm/kg, preferably 0.028 to 0.28 mgm/kg.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 21

Tablets

The tablet composition is compounded from the following ingredients:

| | |
|---|---|
| 5,10-Dihydro-5-[3-(pyrrolidino)-propionyl]-11H-dibenzo-[b,e][1,4]diazepin-11-one hydrochloride | 5.0 parts |
| Lactose | 148.0 parts |
| Potato starch | 65.0 parts |
| Magnesium stearate | 2.0 parts |
| Total | 220.0 parts |

Preparation

An aqueous 10% slurry is prepared with a portion of the potato starch. The active ingredient, the lactose and the remainder of the potato starch are intimately admixed with each other, the mixture is moistened with the potato starch slurry, and the moist mass is granulated through a 1.5 mm-mesh screen. The granulate is dried at 45° C. and then again passed through the screen, admixed with the magnesium stearate, and the composition is compressed in 220 mgm-tablets, each of which is an oral dosage unit composition containing 5 mgm of the active ingredient.

EXAMPLE 22

Coated Tablets

The tablets prepared as described in the preceding example are coated with a thin shell consisting essentially of a mixture of sugar and talcum, and the coated tablets are polished with beeswax.

EXAMPLE 23

Hypodermic Solution

The solution is compounded from the following ingredients:

| | |
|---|---|
| 5,10-Dihydro-5-[3-(pyrrolidino)-propionyl]-11H-dibenzo-[b,e][1,4]diazepin-11-one hydrochloride | 1.0 parts |
| Sodium chloride | 8.0 parts |
| Distilled water q.s. ad | 1000.0 parts by vol. |

Preparation

The active ingredient and the sodium chloride are dissolved in a sufficient amount of distilled water, and the solution is diluted with additional distilled water to the indicated volume. The solution is filtered until free from suspended particles, and the filtrate is filled into 1 cc-ampules which are subsequently sterilized for 20 minutes at 120° C. and then sealed. The contents of each ampule are an injectable solution containing 1 mgm of the active ingredient.

EXAMPLE 24

Suppositories

The suppository composition is compounded from the following ingredients:

| | |
|---|---|
| 5,10-Dihydro-5-[3-(pyrrolidino)-propionyl]-11H-dibenzo-[b,e][1,4]diazepin-11-one hydrochloride | 5.0 parts |
| Suppository base (e.g. cocoa butter) | 1695.0 parts |
| Total | 1700.0 parts |

Preparation

The active ingredient is finely pulverized and homogeneously dispersed in the suppository base which had been melted and cooled to 40° C. 1.7 gm-portions of the mixture are poured at 37° C. into cooled suppository molds and allowed to harden therein. Each suppository is a rectal dosage unit composition containing 5 mgm of the active ingredient.

EXAMPLE 25

Drop Solution

The solution is compounded from the following ingredients:

| | |
|---|---|
| 5,10-Dihydro-5-[3-(pyrrolidino)-propionyl]-11H-dibenzo-[b,e][1,4]diazepin-11-one hydrochloride | 0.5 parts |

| -continued | |
|---|---|
| Methyl—p-hydroxy-benzoate | 0.035 parts |
| Propyl p-hydroxy-benzoate | 0.015 parts |
| Oil of anise | 0.05 parts |
| Menthol | 0.06 parts |
| Ethanol, pure | 10.0 parts |
| Sodium cyclamate | 1.0 parts |
| Glycerin | 15.0 parts |
| Distilled water q.s. ad | 100.0 parts by vol. |

Preparation

The active ingredient and the sodium cyclamate are dissolved in about 70 parts by volume of distilled water, and the glycerin is added. The p-hydroxy-benzoates, the oil of anise and the menthol are dissolved in the ethanol, and the solution is added to the aqueous solution, while stirring. The resulting solution is diluted with distilled water to the indicated volume and filtered until free from suspended particles. 1 ml (about 20 drops) of the solution contains 5 mgm of the active ingredient.

Any one of the other compounds embraced by formula I or a non-toxic, pharmacologically acceptable acid addition salt thereof may be substituted for the particular active ingredient in Examples 21 through 25. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

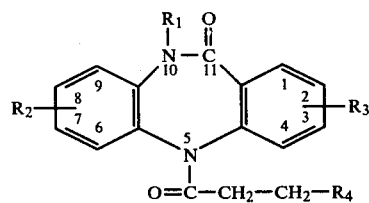

wherein
$R_1$ is hydrogen, methyl or ethyl;
$R_2$ is hydrogen or chlorine;
$R_3$ is hydrogen or chlorine; and
$R_4$ is pyrrolidino, piperidino, 2-methyl-piperidino, 2-ethyl-piperidino, 2,6-dimethyl-piperidino or morpholino;
or a non-toxic, pharmacologically acceptable acid addition salt thereof.

2. A compound of claim 1,
where
$R_1$ is hydrogen or methyl;
$R_2$ and $R_3$ are hydrogen; and
$R_4$ is pyrrolidino or piperidino.

3. A compound of claim 1, which is 5,10-dihydro-5-[3-(pyrrolidino)propionyl]-11H-dibenzo[b,e][1,4]diazepin-11-one or a non-toxic, pharmacologically acceptable acid addition salt thereof.

4. A compound of claim 1, which is 5,10-dihydro-10-methyl-5-[3-(pyrrolidino)propionyl]-11H-dibenzo[b,e][1,4]diazepin-11-one or a non-toxic, pharmacologically acceptable acid addition salt thereof.

5. A compound of claim 1, which is 5,10-dihydro-5-[3-(piperidino)propionyl]-11H-dibenzo[b,e][1,4]diazepin-11-one or a non-toxic, pharmacologically acceptable acid addition salt thereof.

6. A secretion-inhibiting or anti-ulcerogenic pharmaceutical composition consisting essentially of an inert pharmaceutical carrier and an effective secretion-inhibiting or anti-ulcerogenic amount of a compound of claim 1.

7. The method of inhibiting the secretion of gastric fluid or the formation of stomach ulcers in a warm-blooded animal in need thereof, which comprises perorally, parenterally or rectally administering to said animal an effective secretion-inhibiting or anti-ulcerogenic amount of a compound of claim 1.

* * * * *

UNITED STATES PATENT AND TRADEMARK OFFICE
CERTIFICATE OF CORRECTION

PATENT NO. : 4,377,576
DATED : March 22, 1983
INVENTOR(S) : GÜNTHER SCHMIDT and MARIO BERGAMASCHI It is certified that error appears in the above—identified patent and that said Letters Patent is hereby corrected as shown below:

Title page [73]: Correct the assignee's name to read
-- Dr. Karl Thomae Gesellschaft mit beschränkter Haftung --.

Title page [54] and Column 1, 3rd line of title: "[B,E]" should read -- [b,e] --.

Column 1, line 36: "[1,4-" should read -- [1,4]- --.

Column 1, line 37: Delete "]"

Column 2, line 12: "-CH-" should read -- $-CH_2-$ --

Column 2, line 13: Delete "$_2-$"

Column 2, line 50; Column 9, line 18; Column 14, line 2 of Claim 4: "[b-" should read -- [b,- --.

Column 2, line 51; Column 9, line 19; Column 14, line 3 of Claim 4: Delete "," first occurrence.

Column 7, line 27: After "eluant:" delete "e".

Column 7, line 28: "thanol" should read -- ethanol --.

Signed and Sealed this

Eleventh Day of October 1983

[SEAL]

Attest:

GERALD J. MOSSINGHOFF

Attesting Officer    Commissioner of Patents and Trademarks